United States Patent
Shirata et al.

(10) Patent No.: US 9,089,443 B2
(45) Date of Patent: Jul. 28, 2015

(54) MULTI-ARTICULATED LINK KNEE JOINT

(75) Inventors: Takuya Shirata, Tokyo (JP); Yoshiaki Nakaya, Hyogo (JP); Masahiko Okuda, Hyogo (JP)

(73) Assignee: NABTESCO Corporation, Tokyo (JP)

( * ) Notice: Subject to any disclaimer, the term of this patent is extended or adjusted under 35 U.S.C. 154(b) by 0 days.

(21) Appl. No.: 14/352,843

(22) PCT Filed: Mar. 9, 2012

(86) PCT No.: PCT/JP2012/056196
§ 371 (c)(1),
(2), (4) Date: Jun. 26, 2014

(87) PCT Pub. No.: WO2013/132662
PCT Pub. Date: Sep. 12, 2013

(65) Prior Publication Data
US 2015/0032228 A1    Jan. 29, 2015

(51) Int. Cl.
*A61F 2/64* (2006.01)
*A61F 2/76* (2006.01)
*A61F 2/50* (2006.01)
*A61F 2/68* (2006.01)
*A61F 2/70* (2006.01)

(52) U.S. Cl.
CPC . *A61F 2/644* (2013.01); *A61F 2/76* (2013.01); *A61F 2002/5006* (2013.01); *A61F 2002/5084* (2013.01); *A61F 2002/6863* (2013.01); *A61F 2002/704* (2013.01); *A61F 2002/762* (2013.01); *A61F 2002/7625* (2013.01); *A61F 2002/7665* (2013.01)

(58) Field of Classification Search
CPC .............................................. A61F 2002/6863
See application file for complete search history.

(56) References Cited

U.S. PATENT DOCUMENTS

| | | |
|---|---|---|
| 5,383,939 A | 1/1995 | James |
| 6,113,642 A | 9/2000 | Petrofsky et al. |
| 6,517,585 B1 | 2/2003 | Zahedi et al. |
| 6,633,157 B1 | 10/2003 | Yamaki et al. |

(Continued)

FOREIGN PATENT DOCUMENTS

| | | |
|---|---|---|
| EP | 0628296 A2 | 12/1994 |
| GB | 2 328 160 A | 2/1999 |

(Continued)

OTHER PUBLICATIONS

International Search Report from the International Bureau of WIPO for International Application No. PCT/JP2012/056196 dated Jun. 12, 2012 and English translation of the same (4 pages).

(Continued)

*Primary Examiner* — David H Willse
(74) *Attorney, Agent, or Firm* — Fitch Even Tabin & Flannery LLP

(57) ABSTRACT

A multi-articulated link knee joint capable of detecting a bending angle of a knee section without causing problems of an installation space and wiring of a sensor is provided. A four-link knee joint includes a knee section of a four-link mechanism, a fluid cylinder that restrains an action of the knee section, a position detecting device that detects a position of a piston rod with respect to a cylinder tube as an extension and contraction amount of the cylinder, and a computer that acquires a bending angle of the knee section by converting the position detected by the position detecting device.

7 Claims, 8 Drawing Sheets

(56) References Cited

U.S. PATENT DOCUMENTS

| | | | |
|---|---|---|---|
| 6,755,870 B1 | 6/2004 | Biedermann et al. | |
| 2004/0193286 A1 | 9/2004 | Grundei | |
| 2008/0127711 A1* | 6/2008 | Farag | 73/1.11 |

FOREIGN PATENT DOCUMENTS

| JP | H05-212070 A | 8/1993 |
|---|---|---|
| JP | 2000-139974 A | 5/2000 |
| JP | 2001-221653 A | 8/2001 |
| JP | 2001-514925 A | 9/2001 |
| JP | 2002-533161 A | 10/2002 |
| JP | 2004-167106 A | 6/2004 |
| JP | 2004-249102 A | 9/2004 |

OTHER PUBLICATIONS

English Translation of International Preliminary Report on Patentability dated Sep. 9, 2014 for PCT/2012/056196 (5 pages).
Extended European Search Report dated Apr. 10, 2015 for 12870368.3.

* cited by examiner

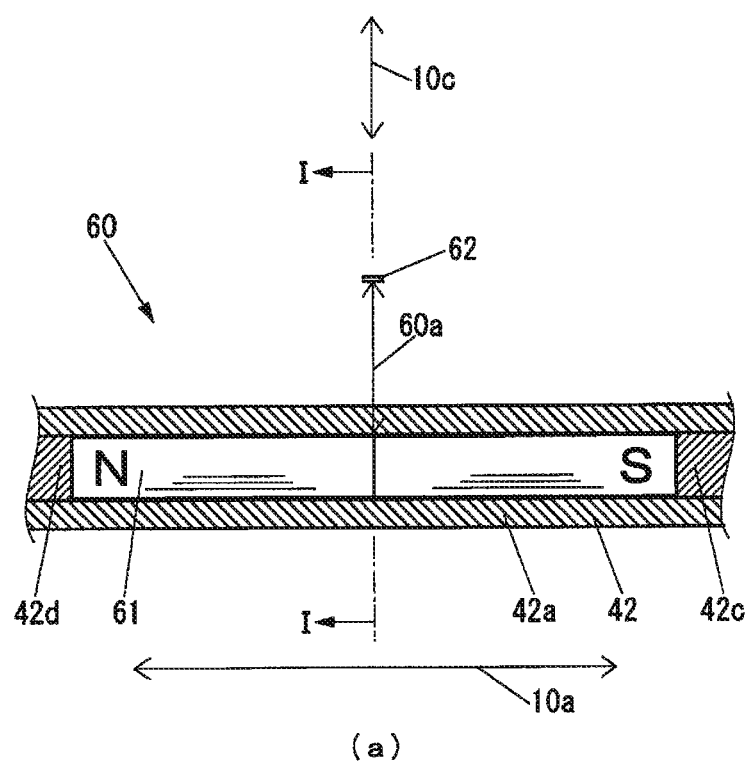
(a)
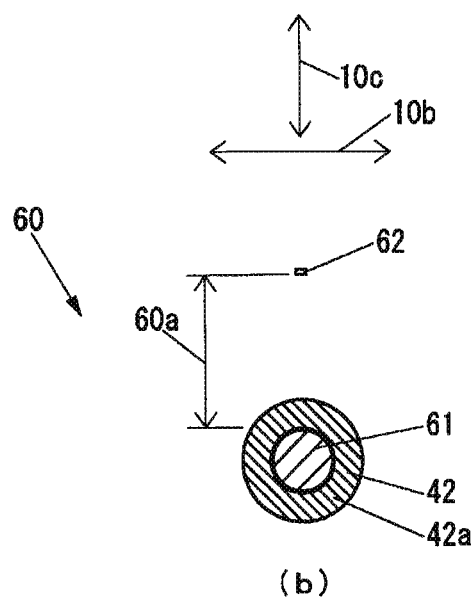
(b)

MULTI-ARTICULATED LINK KNEE JOINT

CROSS-REFERENCE TO A RELATED APPLICATION

This application is a U.S. national phase application filed under 35 U.S.C. §371 of International Application PCT/JP2012/056196, filed on Mar. 9, 2012, which is hereby incorporated herein by reference in its entirety.

TECHNICAL FIELD

The present invention relates to a multi-articulated link knee joint that is a joint including a knee section of a multi-articulated link mechanism.

BACKGROUND ART

Conventionally, as the joints including knee sections, there have been known a single-axis knee joint that is a joint including a knee section with a single axis, and a multi-articulated link knee joint that is a joint including a knee section of a multi-articulated link mechanism.

A multi-articulated link knee joint includes various advantages as compared with a single-axis joint.

For example, in a multi-articulated link knee joint, the position of the instantaneous center of rotation of a knee section is in the position closer to a hip joint as compared with a single-axis knee joint, and therefore, the multi-articulated link knee joint includes the advantage of hardly dropping off at an early stage of standing as compared with the single-axis joint.

Further, in the multi-articulated link knee joint, the lower leg length becomes shorter at the time of bending of the knee section as compared with a single-axis knee joint, and therefore, the distance between the toe and the ground is large when the multi-articulated link knee joint is swung out by walking. Therefore, the multi-articulated link knee joint includes the advantage that the toe is hardly caught by the ground. By the advantage, the multi-articulated link knee joint can obtain beautiful gait without a vertical movement, as compared with a single-axis knee joint.

Further, a multi-articulated link knee joint includes the advantage that the knee cap hardly protrudes at the time of being in a sitting position as compared with a single-axis knee joint.

Further, a multi-articulated link knee joint includes the advantage that even when a user of an artificial leg with knee disarticulation or a long stump uses the multi-articulated link knee joint, the thigh length thereof can be made closer to the thigh length of a well leg, as compared with a single-axis knee joint.

Conventionally, as a multi-articulated link knee joint, there has been known a knee joint that includes a knee section of a multi-articulated link mechanism, an air cylinder that assists an action of the knee section, and a computer that controls an operation of the air cylinder (See Japanese laid-open patent publication No. 2000439974 A and Japanese laid-open patent publication No. 2004-167106 A, for example.).

SUMMARY OF THE INVENTION

The computers in the conventional multi-articulated link knee joints are considered to be more preferable if the computers can control the operation of the air cylinders in accordance with the bending angles of the knee sections.

However, because in a multi-articulated link knee joint, the knee section is not a single-axis knee section in which the position of the center of rotation is constant irrespective of the bending angle, but is the knee section of the multi-articulated link mechanism in which the position of the center of rotation changes in accordance with a change in the bending angle as shown in FIG. 8, and the action range of the knee section is large, the bending angle of the knee section cannot be detected by only detecting the angle that is formed by specific two links connected to each other among the links that configure the knee section. Note that FIG. 8 is an explanatory view of the background art, and is a view showing the change of the position of the center of rotation of a knee section 92 according to the bending angle of the knee section 92 of a multi-articulated link knee joint 90. The multi-articulated link knee joint 90 includes a frame 91 and a knee section 92 of a multi-articulated link mechanism. The knee section 92 includes an upper link 93 including a thigh connection portion 93a for a thigh portion side socket of a user of the artificial leg to be connected, a lower link 94 that is fixed to the frame 91, a front link 95 to which the upper link 93 and the lower link 94 are connected, and a rear link 96 to which the upper link 93 and the lower link 94 are connected. The lower link 94 includes a shaft 94a that rotatably supports the rear link 96. The front link 95 includes a shaft 95a that rotatably supports the upper link 93, and a shaft 95b that is rotatably supported by the lower link 94. The rear link 96 includes a shaft 96a that rotatably supports the upper link 93. A curved line 97 with a plurality of solid-white circles is a line expressing the trajectory of the position of the center of rotation of the knee section 92 according to the change of the bending angle of the knee section 92. The solid-white circles on the curved line 97 represent the positions of the centers of rotation of the knee section 92 in the case in which the angles described in the vicinities thereof being the bending angles of the knee section 92. The state shown in FIG. 8, of the multi-articulated link knee joint 90 is the state of the case of the bending angle of the knee section 92 being 0°.

Further, in the multi-articulated link knee joint, the relative positional relation of the respective links changes significantly with the change of the bending angle of the knee section.

Namely, it is difficult to install the rotational angle sensor for detecting the bending angle of the knee section in the multi-articulated link knee joint, due to various problems such as a problem of an installation space, a problem in wiring, and a problem of design.

Consequently, the present invention has an object to provide a multi-articulated link knee joint capable of detecting a bending angle of a knee section without causing problems of an installation space and wiring of a sensor.

A multi-articulated link knee joint of the present invention includes a knee section of a multi-articulated link mechanism, a cylinder that restrains or assists an action of the knee section, and extension and contraction amount detecting unit that detects an extension and contraction amount of the cylinder, and angle acquiring unit that acquires a bending angle of the knee section by converting the extension and contraction amount that is detected by the extension and contraction amount detecting unit.

According to the above configuration, the multi-articulated link knee joint of the present invention can detect the bending (or extending) angle of the knee section by converting the extension and contraction amount of the cylinder that restrains or assists the action of the knee section. Namely, the multi-articulated link knee joint of the present invention can detect the bending angle of the knee section without causing the problems of the installation space and wiring of the sensor.

Further, the extension and contraction amount detecting unit of the multi-articulated link knee joint of the present invention includes a magnet and a magnetic sensor that detects a position of the magnet, one of the magnet and the magnetic sensor is accommodated in a piston rod of the cylinder, the other one of the magnet and the magnetic sensor is fixed to a cylinder tube of the cylinder, and as the extension and contraction amount, the extension and contraction amount detecting unit may detect a position of the piston rod with respect to the cylinder tube by the magnet and the magnetic sensor.

According to the above configuration, the multi-articulated link knee joint of the present invention detects the position of the piston rod with respect to the cylinder tube as the extension and contraction amount of the cylinder by the magnetic method, and therefore, as compared with the configuration that detects the position of the piston rod with respect to the cylinder tube by a contact or optical method, the possibility of reduction in detection precision by contamination caused by being used can be reduced.

Further, the magnet of the multi-articulated link knee joint of the present invention is accommodated in the piston rod, and the magnetic sensor may be fixed to the cylinder tube.

According to the above configuration, in the multi-articulated link knee joint of the present invention, the magnet is accommodated in the piston rod, and therefore, the magnet can be prevented from being broken by an external force. Further, in the multi-articulated link knee joint of the present invention, arrangement of wiring of the magnetic sensor can be facilitated, as compared with the configuration in which the magnetic sensor is accommodated in the piston rod.

Further, the magnet of the multi-articulated link knee joint of the present invention extends in the extending direction of the piston rod to be longer than a stroke of the cylinder corresponding to an action range of the knee section, a magnetizing direction is the extending direction of the piston rod, and the magnetic sensor may detect a position of the magnet according to a magnitude of a magnetic field generated by the magnet.

According to the above configuration, in the multi-articulated link knee joint of the present invention, the number of magnets needed to detect the position of the piston rod with respect to the cylinder tube of the cylinder can be made one.

Further, the magnet of the multi-articulated link knee joint of the present invention extends in an extending direction of the piston rod to be longer than a stroke of the cylinder corresponding to an action range of the knee section, a magnetizing direction is the extending direction of the piston rod, the magnetic sensor detects a position of the magnet according to a magnitude of a magnetic field generated by the magnet, and in the magnet, a section orthogonal to an extending direction may be circular.

According to the above configuration, in the multi-articulated link knee joint of the present invention, even if the magnet rotates with the axis extending in the extending direction of the magnet as the center, change of the positional relation of the magnet and the magnetic sensor can be restrained. Accordingly, in the multi-articulated link knee joint of the present invention, the magnet does not have to be fixed so as not to rotate in the piston rod, simplification of the configuration can be achieved, and reduction in detection precision of the position of the piston rod with respect to the cylinder tube can be restrained.

The multi-articulated link knee joint of the present invention can detect the bending angle of the knee section without causing problems of the installation space and wiring of the sensor.

BRIEF DESCRIPTION OF THE DRAWINGS

FIG. 5($a$) is a side sectional view of a piston rod, a magnet and a magnetic sensor shown in FIG. 1. FIG. 5($b$) is a sectional view taken along the I-I line of FIG. 5($a$).

DETAILED DESCRIPTION OF THE PREFERRED EMBODIMENT

Hereinafter, one embodiment of the present invention will be described with use of the drawings.

First, a configuration of a four-link knee joint as a multi-articulated link knee joint according to the present embodiment will be described.

Figure 1:
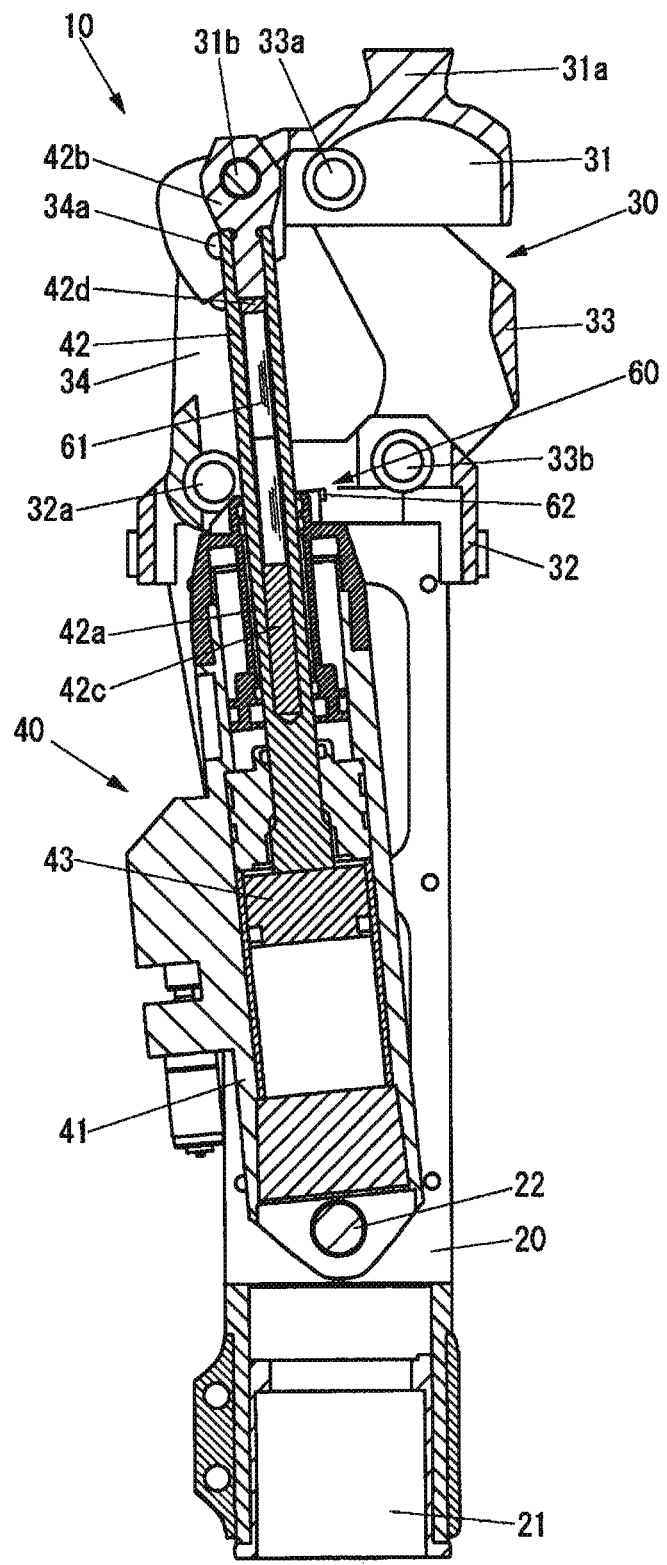
FIG. 1 is a side sectional view of a four-link knee joint according to one embodiment of the present invention in a case in which a bending angle of a knee section is 0°.
Figure 2:
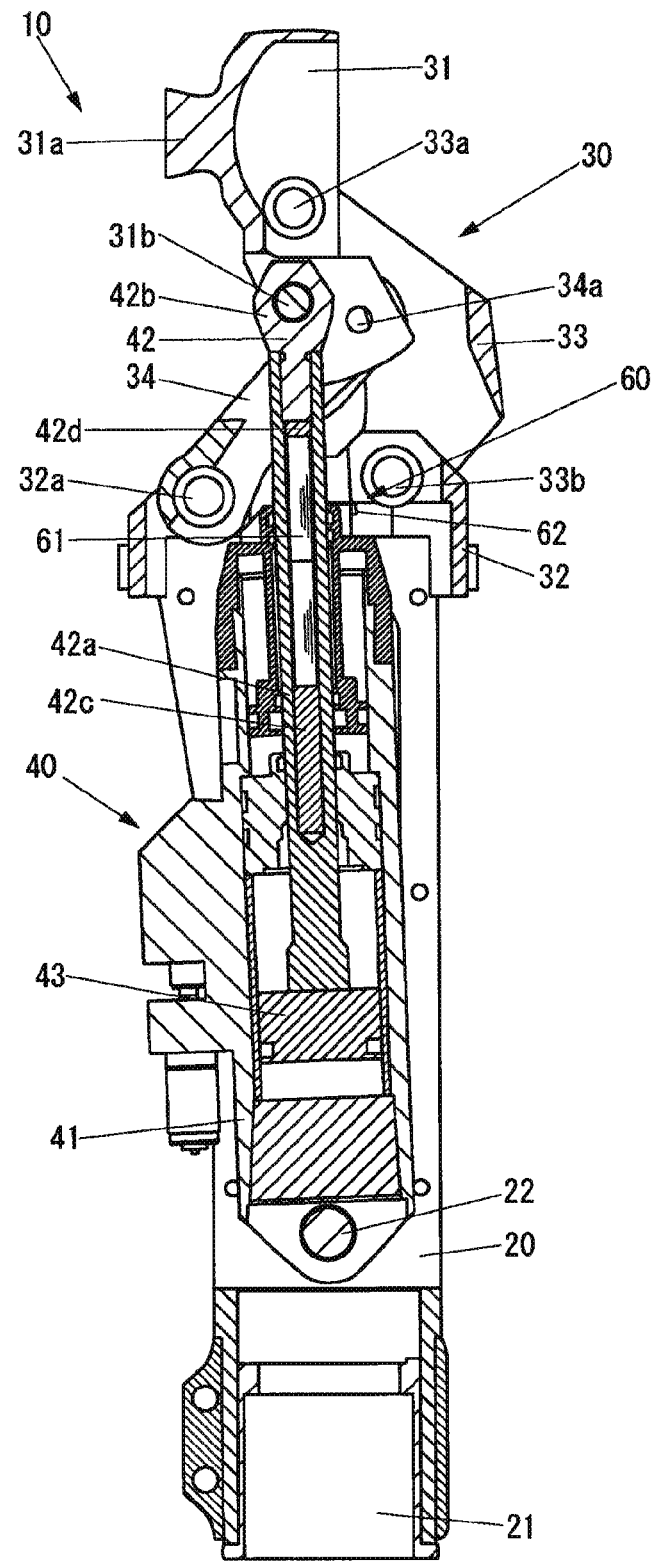
FIG. 2 is a side sectional view of the four-link knee joint shown in FIG. 1 in a case in which the bending angle of the knee section is 90°.
Figure 3:
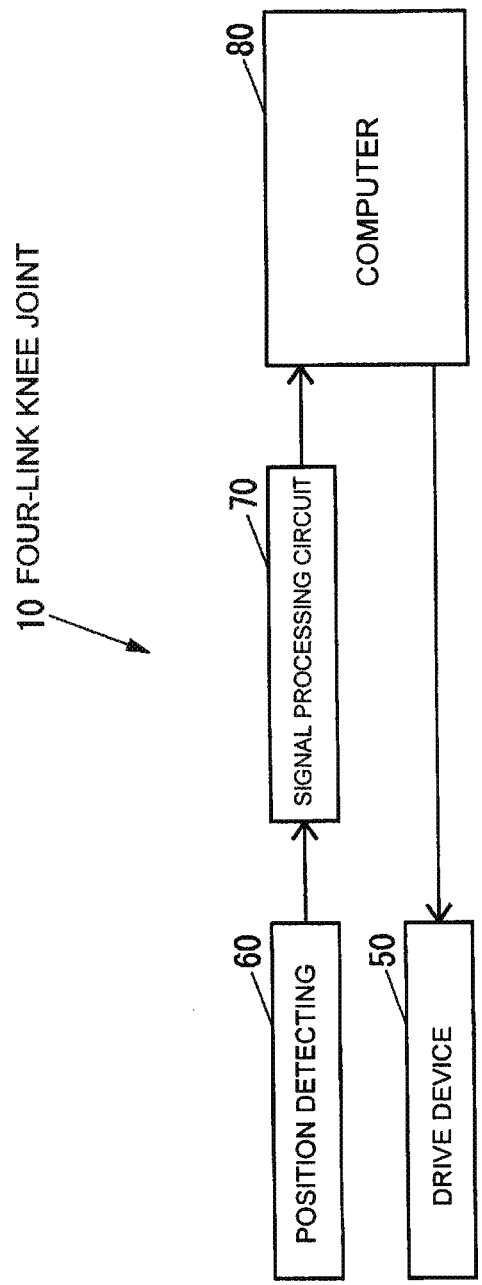
FIG. 3 is a block diagram of the four-link knee joint shown in FIG. 1.

FIG. 1 is a side sectional view of a four-link knee joint 10 according to the present embodiment in a case in which a bending angle of a knee section 30 is 0°. FIG. 2 is a side sectional view of the four-link knee joint 10 in a case in which the bending angle of the knee section 30 is 90°. FIG. 3 is a block diagram of the four-link knee joint 10.

As shown in FIG. 1 to FIG. 3, the four-link knee joint 10 includes a frame 20, the knee section 30 of a four-link mechanism, a fluid cylinder 40 that is cylinder using oil as a working fluid, and restricts an action of the knee section 30 by generating a fluid resistance, a drive device 50 for changing a property of the fluid cylinder 40, a position detecting device 60 as extension and contraction amount detecting unit that detects a position of a piston rod 42 with respect to a cylinder tube 41 of the fluid cylinder 40 as an extension and contraction amount of the fluid cylinder 40, a signal processing circuit 70 that processes a signal that is outputted from the position detecting device 60, a computer 80 that controls the property (the magnitude of the fluid resistance to be generated) of the fluid cylinder 40 by controlling an operation of the drive device 50, and a battery not illustrated that supplies power to various components such as the drive device 50, the signal processing circuit 70 and the computer 80.

Note that the drive device 50, the signal processing circuit 70, the computer 80 and the battery are not illustrated in FIG. 1 and FIG. 2, but are actually mounted on the frame 20 or the fluid cylinder 40.

The knee section 30 is fixed to the frame 20. The frame 20 includes a leg connection portion 21 for a pipe of a leg portion not illustrated to be connected, in an end at an opposite side from a side where the knee section 30 is provided. Further, the frame 20 includes a shaft 22 that rotatably supports the cylinder tube 41. Note that the four-link knee joint 10 forms an artificial leg by being combined with the leg portion.

The knee section 30 includes an upper link 31 including a thigh connection portion 31a for a thigh portion side socket of a user of the artificial leg to be connected, a lower link 32 that is fixed to the frame 20, a front link 33 to which the upper link 31 and the lower link 32 are connected, and a rear link 34 to which the upper link 31 and the lower link 32 are connected. The upper link 31 includes a shaft 31b that rotatably supports the piston rod 42. The lower link 32 includes a shaft 32a that rotatably supports the rear link 34. The front link 33 includes a shaft 33a that rotatably supports the upper link 31, and a shaft 33b that is rotatably supported by the lower link 32. The rear link 34 includes a shaft 34a that rotatably supports the upper link 31.

The shaft 31b is disposed at an upper side from a line connecting the shaft 33a and the shaft 34a. Further, the shaft 22 that rotatably supports the cylinder tube 41 is disposed at a lower side from the frame 20. Accordingly, the fluid cylinder 40 is accommodated so as to be able to extend and contract and swing in an inner side of the frame 20.

The fluid cylinder 40 includes the cylinder tube 41, the piston rod 42 that is movable with respect to the cylinder tube 41, and a piston 43 that is movably accommodated in the cylinder tube 41, and has the piston rod 42 fixed thereto. The piston rod 42 is formed of a non-magnetic material. Further, the piston rod 42 includes a rod main body 42a in which a space for accommodating a magnet 61 that will be described later is formed, a rod end 42b that is fixed to the rod main body 42a, and spacers 42c and 42d that are adjusted to have predetermined lengths to sandwich and fix the magnet 61 inside the piston rod 42. A female screw is formed at the rod main body 42a. A male screw that is combined with the female screw of the rod main body 42a is formed on the rod end 42b.

The position detecting device 60 includes the magnet 61 that is accommodated in the piston rod 42, and a magnetic sensor 62 that is fixed to the cylinder tube 41 and detects a position of the magnet 61. The magnet 61 is an alnico magnet, for example. The magnetic sensor 62 is a sensor that detects a position of the magnet 61 in accordance with the magnitude of a magnetic field that is generated by the magnet 61, and is a Hall element, for example.

Note that in the piston rod 42, the spacer 42c, the magnet 61, and the spacer 42d are accommodated in the rod main body 42a in this sequence, and thereafter, the male screw of the rod end 42b and the female screw of the rod main body 42a are fastened, whereby the magnet 61 is fixed to a predetermined position in an inside thereof.

The computer 80 is an MCU (Micro Control Unit), for example. The computer 80 is configured to acquire the bending angle of the knee section 30, that is, a bending (or extending) angle of the four-link knee joint 10 with respect to the thigh portion of the user of the artificial leg that is connected to the thigh connection portion 31a by converting the position detected by the magnetic sensor 62, and configures angle acquiring unit of the present invention.

Figure 4:
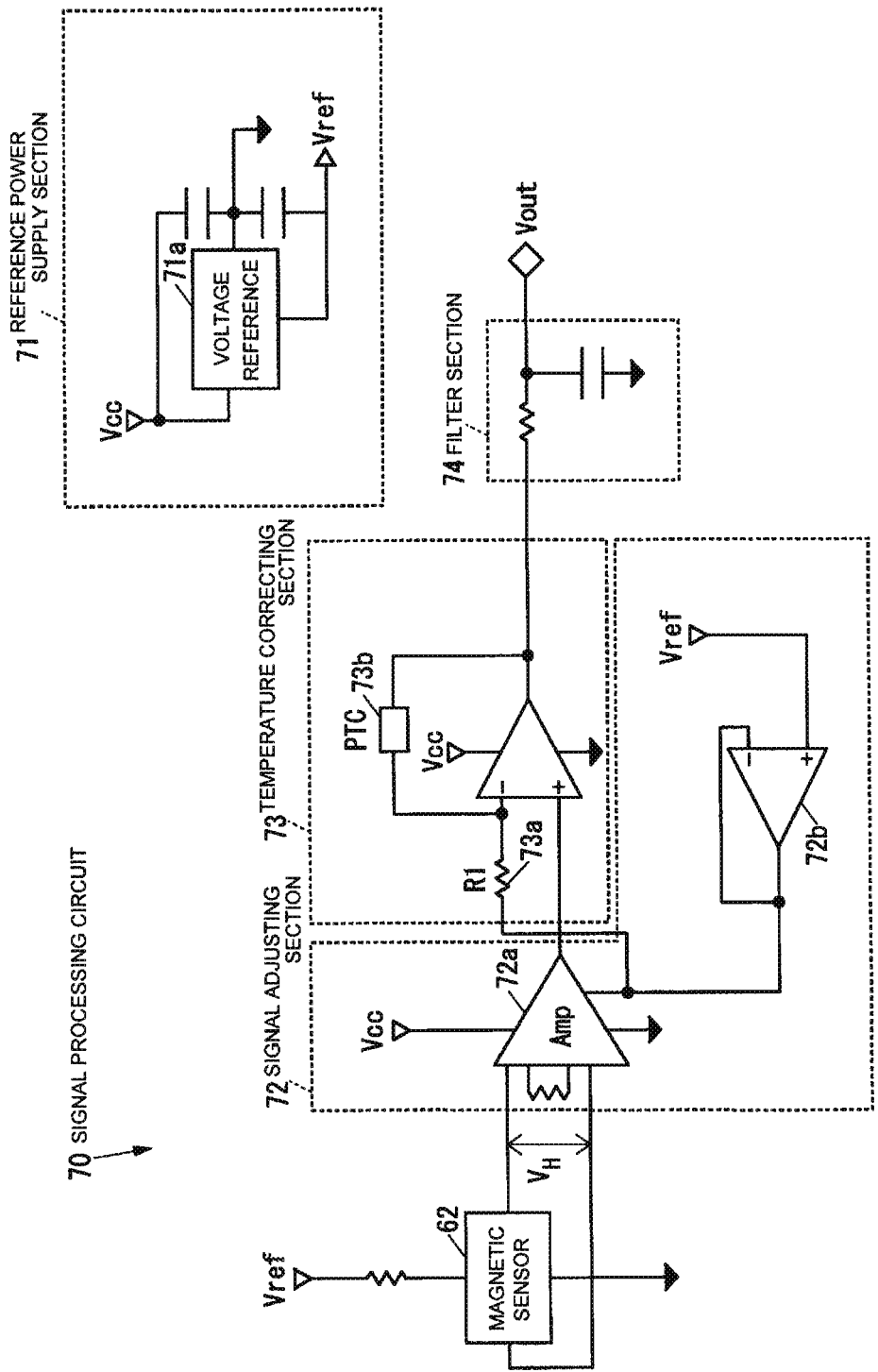
FIG. 4 is a block diagram of a signal processing circuit shown in FIG. 3.

FIG. 4 is a block diagram of the signal processing circuit 70.

As shown in FIG. 4, the signal processing circuit 70 includes a reference power supply section 71 including a voltage reference 71a that generates Vref that is a reference voltage with little temperature change that is inputted into a magnetic sensor 62 from Vcc that is a power supply voltage from a battery not illustrated, a signal adjusting section 72 that adjusts VH that is an output voltage of the magnetic sensor 62, a temperature correcting section 73 that performs correction to a temperature for an output of the signal adjusting section 72 to cancel a temperature characteristic of the magnetic sensor 62, and a filter section 74 that removes noise from an output of the temperature correcting section 73.

The signal adjusting section 72 includes an amplification circuit 72a that amplifies VH, and an offset circuit 72b that adds Vref as an offset voltage to the voltage that is amplified by the amplification circuit 72a. Here, an amplification factor of the amplification circuit 72a is 50-fold, for example.

The temperature correcting section 73 includes a resistor 73a with little change with temperature of electric resistance, and a PTC (Positive Temperature Coefficient) thermistor 73b in which the electric resistance increases in proportion to increase in temperature. Here, the temperature coefficient of the electric resistance of the resistor 73a is ±10 ppm/° C., for example. The temperature coefficient of the electric resistance of the PTC thermistor 73b is approximately 7900 ppm/° C., for example. The temperature coefficient of the electric resistance of the magnetic sensor 62 is approximately −2000 ppm/° C., for example.

Vout that is a signal which is outputted from the signal processing circuit 70 can be expressed as follows by using VH that is the output voltage of the magnetic sensor 62, GAIN that is the amplification factor of the amplification circuit 72a, PTC that is an electric resistance of the PTC thermistor 73b, R1 that is an electric resistance of the resistor 73a, and Vref that is the offset voltage of the offset circuit 72b.

$$Vout = (VH \times GAIN) \times (1 + PTC/R1) + Vref \qquad \text{expression (1)}$$

FIG. 5(a) is a side sectional view of the piston rod 42, the magnet 61 and the magnetic sensor 62. FIG. 5(b) is a sectional view taken along the I-I line of FIG. 5(a).

As shown in FIG. 5, in the magnet 61, a magnetizing direction is an extending direction of the piston rod 42, namely, a direction shown by an arrow 10a. Further, the magnet 61 is a cylindrical magnet in which a section orthogonal to the direction shown by the arrow 10a is circular.

Let's move the magnet 61 in the direction shown by the arrow 10a with respect to the magnetic sensor 62 so that the magnetic sensor 62 changes from a position in a vicinity of one end of the magnet 61 to a position in a vicinity of the other end. In this case, a rate of change of a magnetic field abruptly changes at both the ends of the magnet 61, namely, in the vicinities of magnetic poles of the magnet 61, and therefore, linearity is not recognized between the position of the magnet 61 with respect to the magnetic sensor 62 and the aforementioned Vout. However, since the rate of change of the magnetic field is substantially constant in a vicinity of a central portion of the magnet 61, linearity is recognized between the position of the magnet 61 with respect to the magnetic sensor 62 and the aforementioned Vout. Accordingly, for the purpose of using the range in which the linearity is recognized, as the magnet 61, the magnet is used, which extends in the direction shown by the arrow 10a to be longer than a stroke of the fluid cylinder 40 (See FIG. 1.) in the case of the bending angle of the knee section 30 (see FIG. 1) changing from, for example, 0° to 90°, that is, the stroke of the fluid cylinder 40 corresponding to the action range of the knee section 30. More specifically, in the present embodiment, the magnet 61 has a length about twice as long as the stroke of the fluid cylinder 40 in the case of the bending angle of the knee section 30 changing from 0° to 90°. Note that the length of the magnet 61 may be any length as long as the range in which the aforementioned linearity can be recognized can be used, and does not have to be the length about twice as long as the stroke of the fluid cylinder 40 in the case of the bending angle of the knee section 30 changing from 0° to 90°. However, with consideration being given to the possibility that the position of the magnetic sensor 62 with respect to the magnet 61 in the direction shown by the arrow 10a deviates from the position in design at the time of producing the four-link knee joint 10, the length of the magnet 61 is preferably set to be longer with a certain degree of allowance than the minimum length in which the range with the aforementioned linearity being recognized can be used. The minimum length in which the range with the aforementioned linearity being recognized can be used differs depending on various conditions such as strength of the magnetic force of the magnet 61, the shape of the magnet 61, and a distance of the magnetic sensor 62 with respect to the magnet 61.

Note that a distance 60a between the magnet 61 in a direction orthogonal to the direction shown by the arrow 10a and the magnetic sensor 62 is designed to be a distance in which the linearity between the position of the magnet 61 with respect to the magnetic sensor 62 and the aforementioned Vout becomes high.

It becomes clear by an experiment that in a plane orthogonal to the direction shown by the arrow 10a, a deviation of the position of the magnetic sensor 62 in the direction orthogonal to the straight line connecting a center axis of the magnet 61 and the magnetic sensor 62, namely, in a direction shown by an arrow 10b has a smaller influence on the linearity between the position of the piston rod 42 with respect to the cylinder tube 41 and Vout, as compared with a deviation of the position of the magnetic sensor 62 in the direction of the straight line connecting the center axis of the magnet 61 and the magnetic sensor 62, namely, a direction shown by an arrow 10c. It is conceivable that as compared with the deviation of the position of the magnetic sensor 62 in the direction shown by the arrow 10c, the deviation of the position of the magnetic sensor 62 in the direction shown by the arrow 10b has a small amount of deviation in the deviation of "the distance from the magnet 61" that has an influence on Vout, even if the amounts of deviations from the position in design are the same, and therefore, the influence on the linearity between the position of the piston rod 42 with respect to the cylinder tube 41 and Vout is small.

Figure 6:
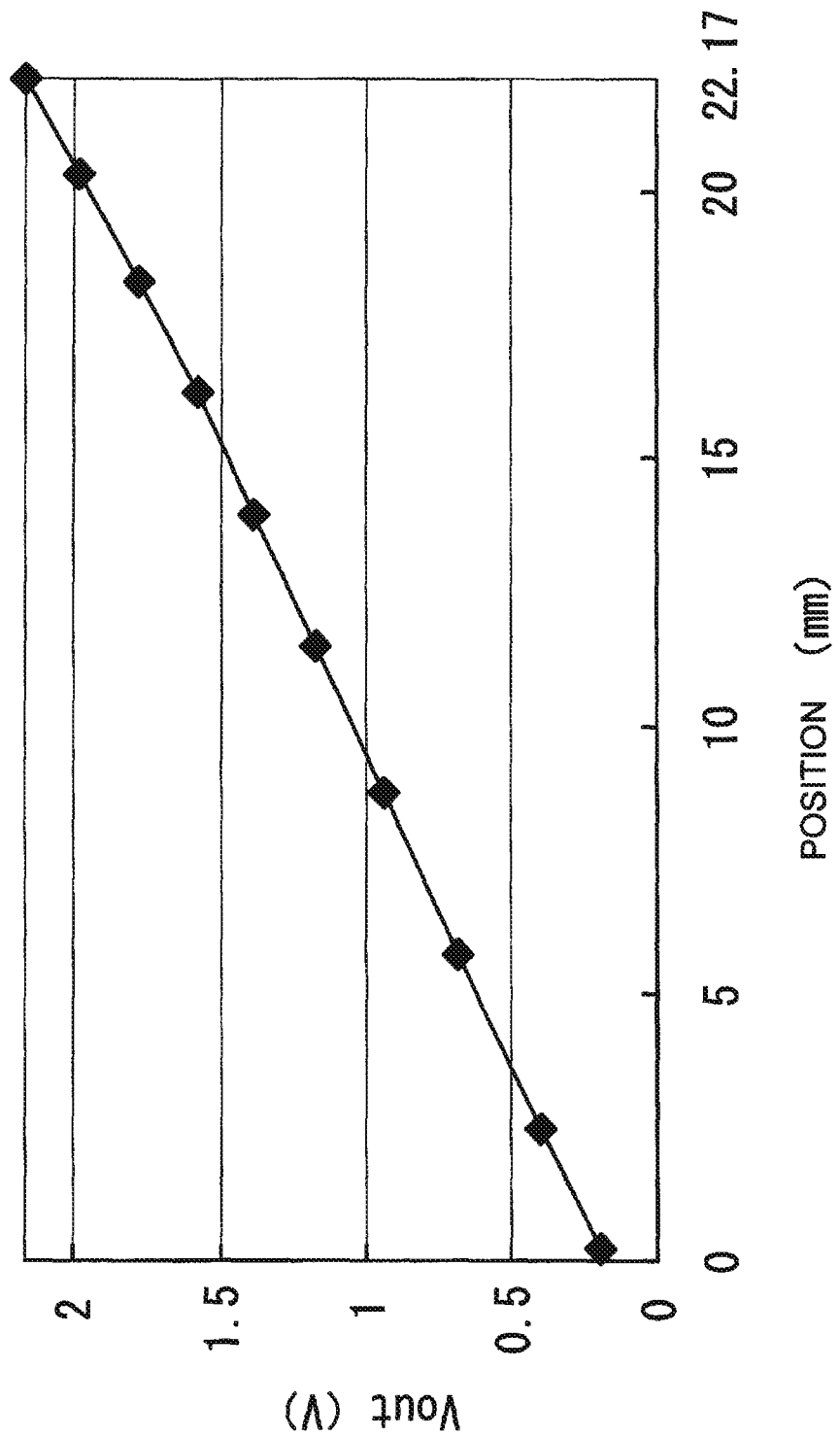
FIG. 6 is a graph showing a relation of a position of the piston rod with respect to a cylinder tube shown in FIG. 1, and Vout.

FIG. 6 is a graph showing a relation of the position of the piston rod 42 with respect to the cylinder tube 41 and Vout. Here, in FIG. 6, positions at 0 mm and 22.17 mm are positions in the case of the bending angles of the knee section 30 being 0° and 90°, respectively.

As shown in FIG. 6, linearity is recognized between the position of the piston rod 42 with respect to the cylinder tube 41, namely, the position of the magnet 61 with respect to the magnetic sensor 62, and Vout.

Accordingly, Lx that is a position of the piston rod 42 with respect to the cylinder tube 41 can be expressed as follows by using 22.17 mm that is a change of the position of the piston rod 42 with respect to the cylinder tube 41 in the case of the bending angle of the knee section 30 changing from 0° to 90°, V0 that is a signal which is outputted from the signal processing circuit 70 when the bending angle of the knee section 30 is 0°, V90 that is a signal which is outputted from the signal processing circuit 70 when the bending angle of the knee section 30 is 90°, and the aforementioned Vout.

$$Lx = 22.27 \times (Vout - V0)/(V90 - V0) \quad \text{expression (2)}$$

Figure 7:
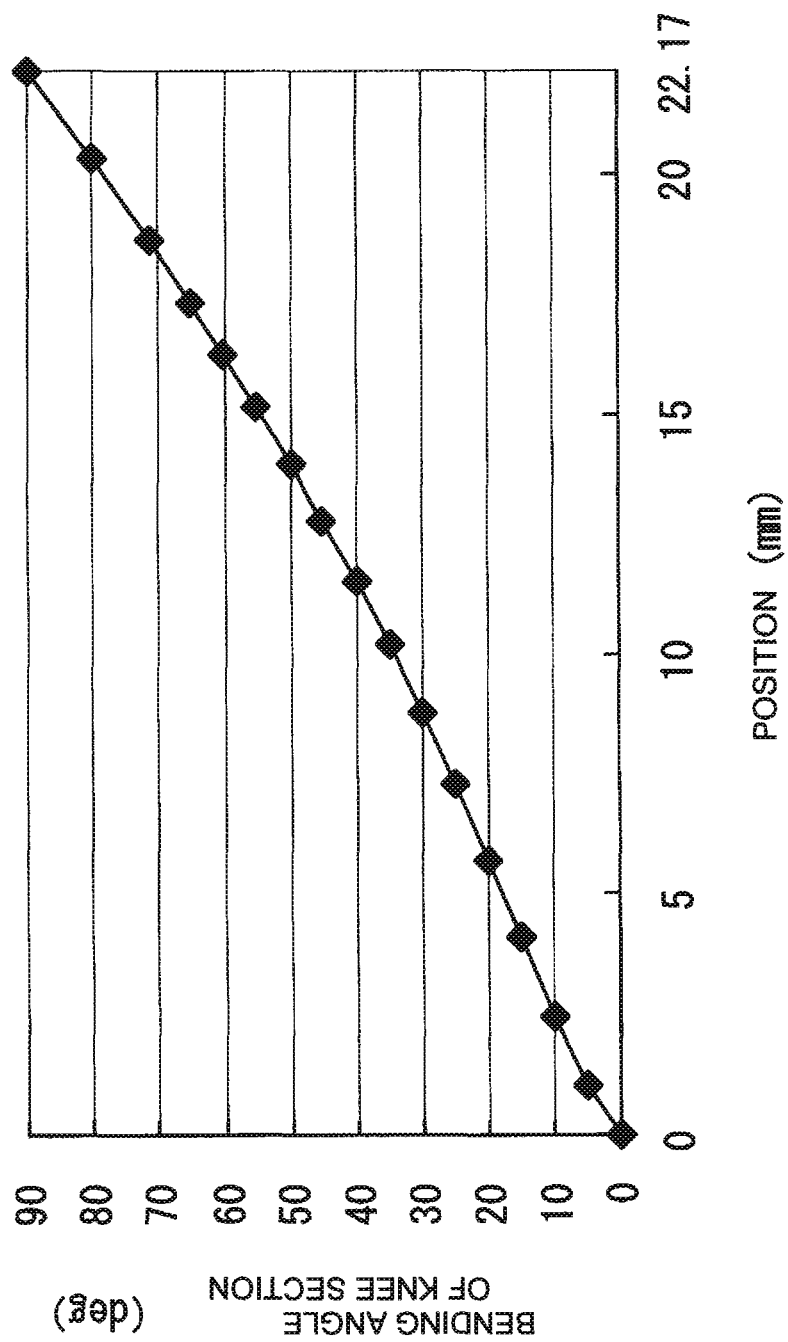
FIG. 7 is a graph showing a relation of the position of the piston rod with respect to the cylinder tube shown in FIG. 1, and the bending angle of the knee section.
Figure 8:
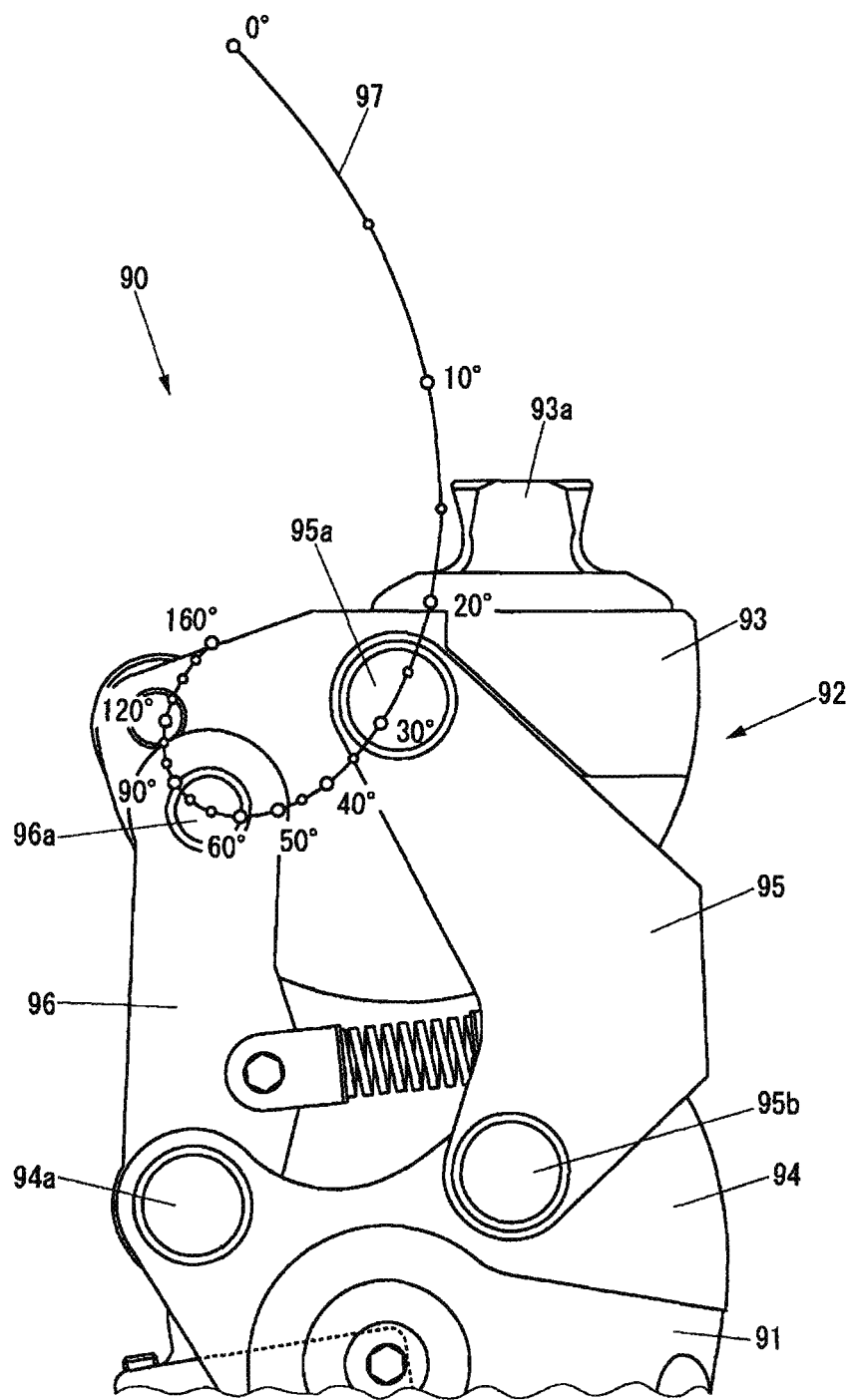
FIG. 8 is an explanatory view of the background art, and is a view showing a change of a position of a center of rotation of a knee section according to a change of a bending angle of the knee section of a multi-articulated link knee joint.

FIG. 7 is a graph showing a relation of the position of the piston rod 42 with respect to the cylinder tube 41 and the bending angle of the knee section 30.

As shown in FIG. 7, the relation of the position of the piston rod 42 with respect to the cylinder tube 41 and the bending angle of the knee section 30 is mechanically set by a structure of the four-link knee joint 10, namely, shaft distances of the shaft 32a, the shaft 33a, the shaft 33b and the shaft 34a that connect the upper link 31, the lower link 32, the front link 33 and the rear link 34, the position of the shaft 31b that rotatably supports the piston rod 42, and the position of the shaft 22 that rotatably supports the cylinder tube 41. Namely, the relations of the positions of the piston rods 42 with respect to the cylinder tubes 41, and the bending angles of the knee sections 30 may differ among the four-link knee joints 10 with different structures, but are the same among the four-link knee joints 10 with the same structures.

For example, Ka that is the bending angle of the knee section 30 can be expressed as follows by using Lx that is the position of the piston rod 42 with respect to the cylinder tube 41.

$$Ka = 0.0041 \times Lx^3 - 0.0773 \times Lx^2 + 3.7559 \times Lx + 0.9886 \quad \text{expression (3)}$$

In this case, based on the aforementioned expression (2) and expression (3), Ka that is the bending angle of the knee section 30 can be expressed as follows by using V0, V90 and Vout described above.

$$Ka = 0.0041 \times [22.17 \times (Vout - V0)/(V90 - V0)]3 - \\ 0.0773 \times [22.17 \times (Vout - V0)/(V90 - V0)]2 + \\ 3.7559 \times [22.17 \times (Vout - V0)/(V90 - V0)] + 0.9886 \quad \text{expression (4)}$$

Next, an action of the four-link knee joint 10 will be described.

The signal processing circuit 70 processes VH that is the output voltage of the magnetic sensor 62 as shown in expression (1) and inputs Vout into the computer 80.

When Vout is inputted into the computer 80 from the signal processing circuit 70, the computer 80 performs processing as shown in expression (4) and generates Ka that is the bending angle of the knee section 30, based on V0 and V90 that are stored in advance and Vout that is inputted from the signal processing circuit 70.

Subsequently, the computer 80 changes the property of the fluid cylinder 40 by controlling the operation of the drive device 50 based on the generated Ka. Note that the computer 80 may also control the operation of the drive device 50 based on information other than Ka.

Accordingly, the action of the knee section 30 is restricted by the fluid cylinder 40. Namely, movement of the knee section 30 to deform is restricted by the fluid resistance generated by the fluid cylinder 40.

Note that in the four-link knee joint 10, V0 and V90 are actually outputted from the signal processing circuit 70 in the state in which the bending angle is made 0° and 90° for each individual, and the V0 and V90 that are outputted are stored in the computer 80, whereby the detection precision of the bending angle Ka of the knee section 30 shown in expression (4) can be kept at each individual. Namely, there is the possibility that the positions of the magnetic sensors 62 with respect to the magnets 61 slightly differ according to the individual four-link knee joints 10 at the time of producing the four-link knee joints 10, but the individual difference of the four-link knee joint 10 like this can be restrained from influencing the detection precision of the bending angle Ka of the knee section 30 by V0 and V90 that are actually outputted being stored in the computer 80.

As described above, the four-link knee joint 10 can detect the bending angle of the knee section 30 by converting the extension and contraction amount of the fluid cylinder 40 that restricts the action of the knee section 30, namely, the position of the piston rod 42 with respect to the cylinder tube 41. Namely, the four-link knee joint 10 can detect the bending (or extending) angle of the knee section 30 according to the method other than the method that uses the rotation angle sensor. Accordingly, the four-link knee joint 10 can detect the bending angle of the knee section without causing problems of the installation space and wiring of the sensor.

Further, the four-link knee joint 10 detects the position of the piston rod 42 with respect to the cylinder tube 41 as the extension and contraction amount of the fluid cylinder 40 by the magnetic method, and therefore, as compared with the configuration that detects the position of the piston rod 42 with respect to the cylinder tube 41 by a contact or an optical method, the possibility of reduction in detection precision by contamination that is caused by being used can be reduced. Furthermore, the magnet 61 is accommodated in the piston rod 42, and therefore, the magnet 61 is not broken or worn by an external force and contact with the other portions in the four-link knee joint 10. Further, in the four-link knee joint 10, the magnetic sensor 62 is not accommodated in the piston rod 42, and therefore, as compared with the configuration in which the magnetic sensor 62 is accommodated in the piston rod 42, arrangement of wiring of the magnetic sensor 62 can be facilitated.

Note that the four-link knee joint 10 may detect the position of the piston rod 42 by optically detecting white colors, black colors or the like that are alternately colored in a longitudinal direction on an outer periphery of the piston rod 42, for example, or magnetically detecting N-poles and S-poles that are alternately magnetized. Further, the cylinder tube 41 is made non-magnetic, a magnet is contained in the piston 43, a plurality of magnetic sensors are disposed along the moving direction of the piston 43, and thereby, the position of the piston 43 may be detected. Further, without being limited to this, the position of the piston rod 42 or the piston 43 with respect to the cylinder tube 41 may be detected by a contact method, or another optical or magnetic method. Namely, any method can be adopted, as long as the position of the piston rod 42 or the piston 43 with respect to the cylinder tube 41, namely, the extension and contraction amount of the fluid cylinder 40 can be measured.

In the four-link knee joint 10, the number of magnets that are needed to detect the position of the piston rod 42 with respect to the cylinder tube 41 of the fluid cylinder 40 can be made one, because the magnet 61 extends in the extending direction of the piston rod 42 to be longer than the stroke of the fluid cylinder 40 in the case of the bending angle of the knee section 30 changing from 0° to 90°, the magnetizing direction of the magnet 61 is the extending direction of the piston rod 42, and the magnetic sensor 62 detects the position of the magnet 61 in accordance with the magnitude of the magnetic field generated by the magnet 61.

In the four-link knee joint 10, the section of the magnet 61, which is orthogonal to the extending direction, is circular, and therefore, even if the magnet 61 rotates with the axis extending in the extending direction of the magnet 61 as the center by the piston rod 42 rotating with respect to the cylinder tube 41, change of the positional relation of the magnet 61 and the magnetic sensor 62 can be restrained. Accordingly, in the four-link knee joint 10, the magnet 61 does not have to be fixed so as not to rotate in the piston rod 42, the configuration can be simplified, and reduction in detection precision of the position of the piston rod 42 with respect to the cylinder tube 41 can be restrained.

Further, in the four-link knee joint 10, the section of the magnet 61, which is orthogonal to the extending direction, is circular, and therefore, even if the magnet 61 rotates with the axis extending in the extending direction of the magnet 61 as the center, as compared with the state of the magnet 61 that is planned, at the time of assembly, such as, at the time of the magnet 61 being incorporated in the piston rod 42, at the time of the fluid cylinder 40 being connected to the frame 20 and the knee section 30, and at the time of the magnetic sensor 62 being mounted to the fluid cylinder 40, the possibility that the positional relation of the magnet 61 and the magnetic sensor 62 differs from the positional relation that is planned can be reduced. Accordingly, in the four-link knee joint 10, the detection precision of the position of the piston rod 42 with respect to the cylinder tube 41 can be restrained from being reduced when the four-link knee joint 10 is assembled.

Note that in the magnet 61, the section orthogonal to the extending direction does not have to be circular. For example, when the magnet 61 is fixed so as not to rotate in the piston rod 42, and when the detection precision of the position of the piston rod 42 with respect to the cylinder tube 41 may be relatively low, the magnet 61 may be a prismatic magnet instead of a cylindrical magnet.

The mechanism of the knee section of the present invention is a four-link mechanism in the present embodiment, but may be a multi-articulated link mechanism other than the four-link mechanism.

The cylinder of the present invention is a fluid cylinder using hydraulic pressure in the present embodiment, but may be, for example, a fluid cylinder using a gas such as air. In this case, as an entire artificial leg, control of a swing phase is performed instead of a stance phase, the fluid cylinder generates a repulsive force (namely, a force that assists extension) instead of fluid resistance, and the repulsive force is controlled by the computer.

The extension and contraction amount detecting unit of the present invention includes the magnet 61 accommodated in the piston rod 42, and the magnetic sensor 62 that is fixed to the cylinder tube 41, and detects the position of the magnet 61. However, the extension and contraction amount detecting unit of the present invention may be such that a magnetic sensor is accommodated in the piston rod 42 and a magnet is fixed to the cylinder tube 41.

The invention claimed is:

1. A multi-articulated link knee joint, comprising:
a knee section of a multi-articulated link mechanism;
a cylinder that restrains or assists an action of the knee section;
extension and contraction amount detecting unit that detects an extension and contraction amount of the cylinder; and
angle acquiring unit that acquires a bending angle of the knee section by converting the extension and contraction amount that is detected by the extension and contraction amount detecting unit,
wherein the extension and contraction amount detecting unit includes a magnet and a magnetic sensor that detects a position of the magnet,
a piston rod of the cylinder is formed of a non-magnetic material, and has a space that accommodates the magnet, in an inside thereof,
the magnet is accommodated in the space of the piston rod of the cylinder, and extends in an extending direction of the piston rod to be longer than a stroke of the cylinder corresponding to an action range of the knee section, and a magnetizing direction is the extending direction of the piston rod, a length of the magnet is a length in a range in which at least linearity of the extension and contraction amount detecting unit is recognized, in the stroke of the cylinder, the magnetic sensor is fixed to a cylinder tube of the cylinder, and detects a position of the magnet according to a magnitude of a magnetic field that is generated by the magnet, and the extension and contraction amount detecting unit detects a position of the piston rod with respect to the cylinder tube by the magnet and the magnetic sensor, as the extension and contraction amount.

2. The multi-articulated link knee joint according to claim 1,
wherein the piston rod comprises
a rod main body provided with the space, and
a rod end that is fixed to the rod main body, and
the magnet is fixed into the space by a spacer and the rod end.

3. The multi-articulated link knee joint according to claim 1,
wherein the length of the magnet is set based on at least one of strength of a magnetic force of the magnet, a shape of the magnet, and a distance of the magnetic sensor with respect to the magnet.

4. The multi-articulated link knee joint according to claim 1,
wherein the length of the magnet is twice as long as the stroke.

5. The multi-articulated link knee joint according to claim 1,
wherein in the magnet, a section orthogonal to an extending direction is circular.

6. The multi-articulated link knee joint according to claim 1,
wherein the magnetic sensor includes a temperature correcting section for canceling a temperature characteristic.

7. The multi-articulated link knee joint according to claim 6,
wherein the temperature correcting section includes
a resistor capable of ignoring a temperature change by electric resistance, and
a thermistor with the electric resistance increasing in proportion to an increase in a temperature.

* * * * *